United States Patent
Looper et al.

(10) Patent No.: US 10,286,194 B2
(45) Date of Patent: May 14, 2019

(54) METHOD OF TREATING PLEURAL EFFUSION

(75) Inventors: Anthony Looper, Lake Zurich, IL (US); Jeffrey Schmitt, Trumbull, CT (US); Monica Sanders, Oak Park, IL (US); Alain Tremblay, Calgary (CA)

(73) Assignees: CAREFUSION 2200, INC., San Diego, CA (US); UTI Limited Partnership, Calgary, AB (CA)

( * ) Notice: Subject to any disclaimer, the term of this patent is extended or adjusted under 35 U.S.C. 154(b) by 135 days.

(21) Appl. No.: 13/696,484

(22) PCT Filed: May 5, 2011

(86) PCT No.: PCT/US2011/035294
§ 371 (c)(1),
(2), (4) Date: May 20, 2013

(87) PCT Pub. No.: WO2011/140298
PCT Pub. Date: Nov. 10, 2011

(65) Prior Publication Data
US 2013/0261598 A1    Oct. 3, 2013

Related U.S. Application Data

(60) Provisional application No. 61/332,579, filed on May 7, 2010.

(51) Int. Cl.
*A61M 31/00* (2006.01)
*A61M 27/00* (2006.01)
*A61M 1/00* (2006.01)

(52) U.S. Cl.
CPC .......... *A61M 27/00* (2013.01); *A61M 1/0031* (2013.01); *A61M 31/00* (2013.01); *A61M 2210/101* (2013.01)

(58) Field of Classification Search
USPC .................................................. 604/317, 319
See application file for complete search history.

(56) References Cited

U.S. PATENT DOCUMENTS

| | | | |
|---|---|---|---|
| 3,960,153 A | 6/1976 | Carey et al. | |
| 5,484,401 A | 1/1996 | Rodriguez et al. | |
| 6,132,415 A | 10/2000 | Finch et al. | |
| 2009/0043270 A1* | 2/2009 | Noyce et al. | 604/327 |
| 2009/0247983 A1* | 10/2009 | Tremblay et al. | 604/502 |

FOREIGN PATENT DOCUMENTS

WO    WO 2009-059341 A1    5/2009

OTHER PUBLICATIONS

Lubin, M. F. (2009). Medical management of the surgical patient: A textbook of perioperative medicine. Cambridge: Cambridge University Press.*
Ferrell, B., & Coyle, N. (2006). Textbook of palliative nursing. Oxford: Oxford University Press.*
(Continued)

*Primary Examiner* — Bradley J Osinski
*Assistant Examiner* — Nilay J Shah
(74) *Attorney, Agent, or Firm* — Arent Fox LLP

(57) ABSTRACT

The present invention provides methods of treating pleural effusion in a subject, comprising removing fluid from the pleural space at an increased frequency, as compared to previous methods.

12 Claims, 2 Drawing Sheets

(56) References Cited

OTHER PUBLICATIONS

Seijo, L., Campo, A., Alcaide, A.B., del Mar Lacunza, M., Armendáriz, A. C., & Zulueta, J. J. (2006). Outpatient management of malignant pleural effusion using a tunneled pleural catheter: Preliminary experience. Archivos de Bronconeumología ((English Edition)), 42(12), 660-662.*

Tettey, M., Sereboe, L., Edwin, F., & Frimpong-Boateng, K. (2005). Tetracycline Pleurodesis for Malignant Pleural Effusion—A Review of 38 Cases. Ghana Medical Journal, 39(4), 128-131.*

Havelock, T., Teoh, R., Laws, D., & Gleeson, F. (2010). Pleural procedures and thoracic ultrasound: British Thoracic Society pleural disease guideline 2010. Thorax, 65(Suppl 2), i61-i76.*

Maritato, K. C., Colon, J. A., & Kergosien, D. H. (2009). Pneumothorax. Compendium (Yardley, PA), 31(5), 232-42.*

Bayram, A. S., Köprücüoğlu, M., Aygün, M., & Gebitekin, C. (2008). Pleurovenous shunt for treating refractory benign pleural effusion. European Journal of Cardio-Thoracic Surgery, 33(5), 942-943.*

Muir, J, et al. "Utilisation De La Doxycycline Intrapleurale Par Lavage-Drainage Dans Les Epanchements Recifivants d'Origine Neoplasique." Mal. Resp., vol. 4, 1987, pp. 29-33. (Year: 1987).*

Walker-Renard, Pamela B., Leigh M. Vaughan, and Steven A. Sahn. "Chemical pleurodesis for malignant pleural effusions." Annals of internal medicine 120.1 (1994): 56-64. (Year: 1994).*

Dixit, Ramakant, Kalpana Dixit, and Rani Bansal. "Intrapleural streptokinase in multiloculated malignant pleural effusion." Indian Journal of Chest Diseases and Allied Sciences 46.1 (2004): 59-62. (Year: 2004).*

Non-patent Literature Translation: Utilisation De La Doxycycline Intrapleurale Par Lavage-Drainage Dans Les Epanchements Recifivants d'Origine Neoplasique (Year: 2018).*

Chinese Office Action, dated Jul. 1, 2014, issued in Chinese Application No. 201180022934.X.

\* cited by examiner

METHOD OF TREATING PLEURAL EFFUSION

CROSS-REFERENCE TO RELATED APPLICATION

This application is a National Stage entry of International Application No. PCT/US2011/035294 filed May 5, 2011, which claims priority to U.S. Provisional Patent Application No. 61/332,579 filed May 7, 2010, the disclosure of the prior applications are hereby incorporated in their entirety by reference.

FIELD OF THE INVENTION

The present invention provides methods of treating pleural effusion in a subject, comprising removing fluid from the pleural space at an increased frequency, as compared to previous methods.

BACKGROUND OF THE INVENTION

The pleural cavity and the pleura serve an important function of aiding in the optimal functioning of the lungs during respiration. The pleural cavity consists of the visceral pleural layer which covers the lungs, the parietal pleural layer that lines the chest wall, and the thin layer of fluid that separates the two. Diseases affecting the pleural cavity and pleura include pleural effusions and pneumothorax. Pleural effusions involve the build-up of excess fluid around the lungs, and pleural effusions result from accumulation of fluid in the pleural space. Pleural effusions can be associated with conditions such as cancer, tuberculosis, congestive heart failure, pneumonia, pulmonary emboli, viral disease, cirrhosis, post-coronary artery bypass graft surgery, gastrointestinal disease, tuberculosis pancreatitis, and mesothelioma. Pneumothorax occurs when air or gas is present in the pleural cavity.

Patients with pleural diseases such as symptomatic pleural effusions or pneumothorax are typically treated with thoracentesis to remove fluid or air, and/or chemical or mechanical pleurodesis.

Removal of excessive fluids from the pleural space is an important part of treating symptomatic pleural effusions. An excess of fluids in the pleural space can result in chest pain, shortness of breath upon mild exertion and/or at rest, and general discomfort in a patient. In addition to relieving these symptoms, the removal of excessive pleural fluid is important, as the fluid occasionally becomes infected and can cause further complications in a patient.

Pleurodesis is also a common treatment for patients with recurrent symptomatic pleural effusions. Pleurodesis involves chemical or mechanical irritation of the parietal and/or visceral layers of the pleura in order to close off the pleural space and prevent further fluid and/or air accumulations. Pleurodesis is typically characterized by the creation of fibrous adhesions between the parietal and visceral layers of the pleura. Chemical pleurodesis can be achieved with the insertion of sclerosing agents, typically by catheter, into the pleural space. Sclerosing agents include talc, tetracycline, doxycycline, minocycline, doxorubicin, povidone iodine, bleomycin, $TGF_\beta$ and silver nitrate.

The pleural fluid of patients with symptomatic pleural effusions is often aspirated or removed for diagnostic testing. For example, a diagnostic pleural fluid sample may be aspirated from the pleural space with a needle and syringe and analyzed for the presence of proteins, enzymes, and microbes. In addition, the cytology and the pH of the fluid may be tested. Maskell et al. "BTS Guidelines for the Investigation of a Unilateral Pleural Effusion in Adults," *Thorax*, 2003, 58: ii8-ii17.

Removal of fluid from the pleural space should be monitored carefully to reduce the possibility of adverse effects, such as re-expansion pulmonary edema. Typically, fluid removal should not exceed about 1.5 L per sitting. However, based on the individual patient, greater amounts of pleural fluid may be removed. Feller-Kopman D., "Large-volume Thoracentesis and the Risk of Re-expansion Pulmonary Edema," *Ann Thorac Surg*, 2007; 84(5): 1656-1661.

Some patients, including patients with recurrent malignant pleural effusions, require periodic removal of pleural fluid, to relieve symptoms and decrease the risk of medical complications. The removal of pleural fluid can be done at the hospital on an in-patient basis, or on an outpatient basis. After the removal of excessive pleural fluid, patients often experience an increase in total lung capacity and an improvement in their symptoms. Antony et al. "Management of Malignant Pleural Effusions," *Eur Respir J.* 2001; 18: 402-419.

Typically, the frequency at which patients receive treatments of pleural fluid removal is based on their symptoms. For example, outpatients often receive an initial treatment of pleural fluid removal, and they receive subsequent treatments based on when their symptoms return. Patients typically receive treatments every 2 to 7 days. Alternatively, patients receiving inpatient pleurodesis typically require only one treatment. However, there are problems with either approach. Patients receiving outpatient fluid removal treatments can achieve "spontaneous" pleurodesis, but in a relatively long timeframe and at unsatisfactory success rates. Patients receiving inpatient pleurodesis undergo a procedure that is often painful, requires a 4-7 day hospital stay, and has a relatively high recurrence rate. One theory that attempts to explain this is that the rapid re-accumulation of fluid in the pleural space makes it more difficult for the parietal and visceral layers of the pleura to adhere and close off the pleural space.

There is a need in the art for a method of quickly and successfully treating pleural effusion in subjects, allowing patients to obtain relief from symptoms quickly and safely.

All references are incorporated herein by their entirety.

SUMMARY OF THE INVENTION

The present invention relates to a method of treating pleural effusion in a subject, comprising: administering two or more treatments comprising removing an amount of fluid from the pleural space of the subject, wherein the treatments are administered at a frequency of every about 12 to about 72 hours until 2 or more consecutive treatments each remove less than 300 mL of fluid.

The present invention also provides a kit comprising: a device for removing fluid from the pleural space of a subject, and instructions for use.

Other novel features and advantages of the present invention will become apparent to those skilled in the art upon examination of the following or upon learning by practice of the invention.

DETAILED DESCRIPTION OF THE INVENTION

The present invention relates to a method of treating pleural effusion in a subject, comprising: administering two or more treatments comprising removing an amount of fluid from the pleural space of the subject, wherein the treatments are administered at a frequency of every about 12 to about 72 hours until 2 or more consecutive treatments each remove less than 300 mL of fluid.

Figure 1:
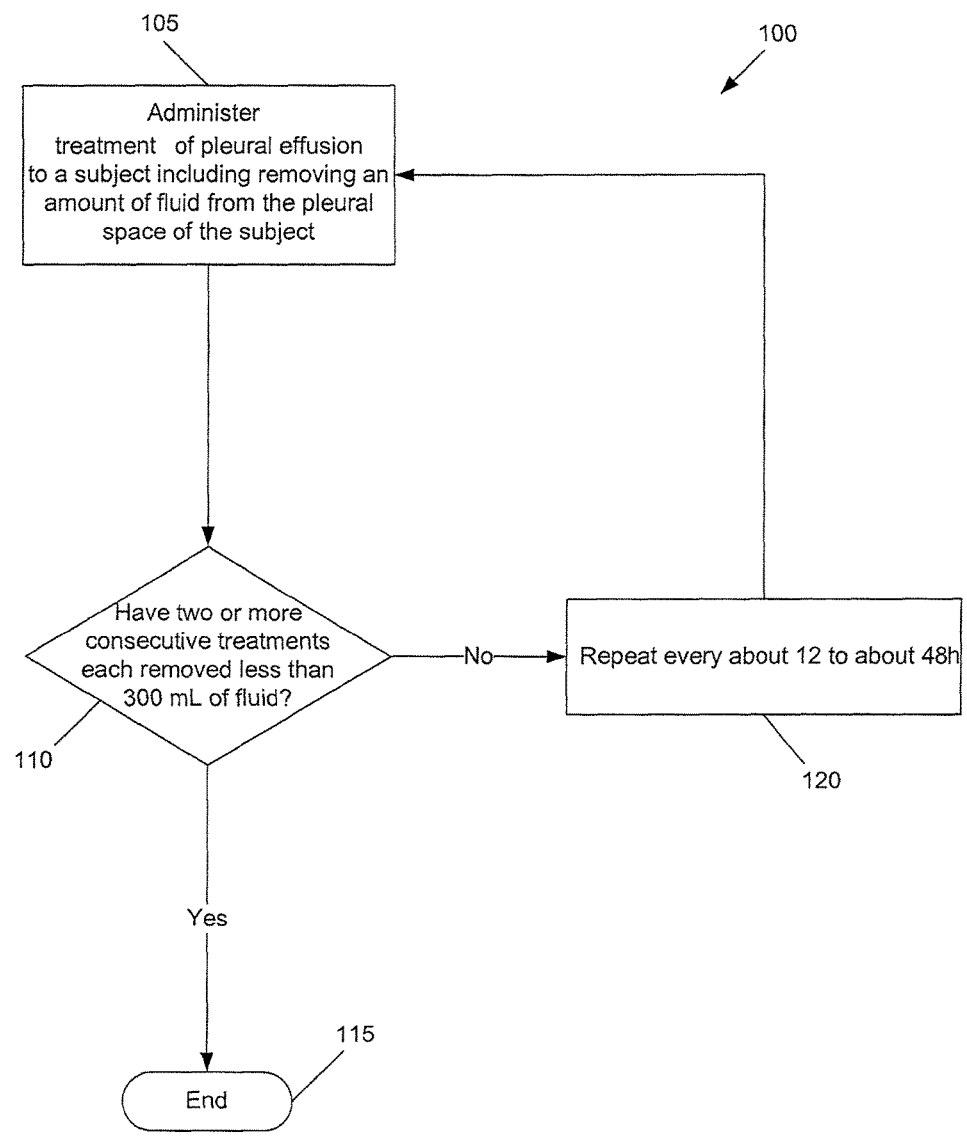
FIG. 1 is a flowchart of a method of treating pleural effusion according to various example aspects of the invention.

With reference to FIG. 1, the treatments 100 of the present invention involve removal of an amount of fluid from the pleural space of a subject having pleural effusion 105. The removal of the fluid 105 may be accomplished by any known method in the art and by any device known in the art. Examples of devices include, but are not limited to catheters, chest tubes, syringes, or needles. Preferably the fluid is removed by a catheter, more preferably a pleural catheter. In preferred embodiments, the treatments are conducted on an outpatient basis, in patients having an indwelling pleural catheter, such as the PLEURX® Pleural Catheter, marketed by Carefusion. Putnam et al. 'Outpatient Management of Malignant Pleural Effusion by a Chronic Indwelling Pleural Catheter,' Ann Thorac Surg 2000; 69:369-375. Warren et al. 'Identification of clinical factors predicting PleurX® catheter removal in patients treated for malignant pleural effusion.' *European Journal of Cardio-Thoracic Surgery* 2008; 33(1): 89-94.

The amount of fluid removed from the pleural space of a patient during each treatment should be determined by the health care professional. The appropriate amount of fluid to be removed, and the duration of each treatment, will vary based on the severity of the patient's condition, as well as the patient's age, weight, comorbidities, and other such factors. In preferred embodiments, no more than 2 liters, and preferably no more than 1 liter, is removed from the pleural space during each treatment. In preferred embodiments, fluid should be removed at a rate of less than 600 mL/min, more preferably less than 500 mL/min, and most preferably between 25 and 400 mL/min. In some embodiments, the duration of each treatment period is less than 2 hours, preferably less than 1 hour, and more preferably less than 20 minutes.

After an initial treatment of fluid removal, one or more subsequent treatments may be administered. The subsequent treatments preferably may be administered at a frequency of every about 12 to about 72 hours, preferably about 12 to about 48 hours 120, more preferably about 24 hours. The subsequent treatments should be administered until 2 or more consecutive treatments each remove less than about 300 mL of fluid, preferably less than about 250 mL of fluid, more preferably less than about 150 mL of fluid, and most preferably less than about 100 mL of fluid. In preferred embodiments, as shown in FIG. 1, the subsequent treatments are administered until 2 or more consecutive treatments each remove less than about 300 mL of fluid 110, preferably less than about 250 mL of fluid, more preferably less than about 150 mL of fluid, and most preferably less than about 100 mL of fluid.

After the patient is administered 2 or more consecutive treatments in which the amount of fluid removed from the pleural space is below the selected threshold, the administration of any necessary additional treatments may occur on a less frequent basis 115. For example, any necessary additional treatments may occur less frequently than previously administered 115. In some embodiments, any necessary additional treatments may occur at a frequency of every 3 or more days 115.

In some embodiments, a pleurodesis treatment may be administered in addition to the fluid removal treatment. The pleurodesis treatment may be any treatment known in the art which creates pleurodesis. The pleurodesis treatment may be a mechanical pleurodesis treatment or a chemical pleurodesis treatment. The chemical pleurodesis treatment may comprise administration of one or more sclerosing agents. Sclerosing agents include but are not limited to: talc, tetracycline, doxycycline, minocycline, doxorubicin, povidone iodine, bleomycin, $TGF_\beta$ and silver nitrate. In some embodiments, the sclerosing agent is silver or a salt of silver.

The methods of the present invention may be administered to any subject in need thereof, preferably mammalian subjects. Preferably, the mammalian subjects are selected from the group consisting of: humans, sheep, dogs, cats, cows, and horses. Preferably the mammalian subject is a human.

Figure 2:
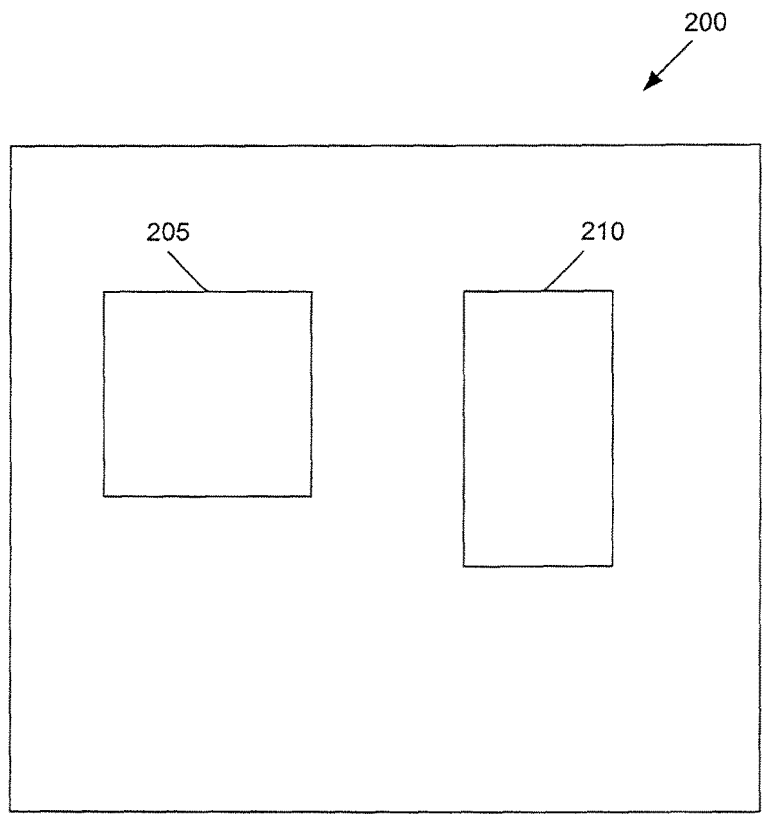
FIG. 2 is schematic representation of a kit according to various example aspects of the invention.

With respect to FIG. 2, the present invention also provides for a kit 200 comprising: a device 205 for removing fluid from the pleural space of a subject, and instructions 210 for use. The instructions for use comprise instructions for the method of treating pleural effusion, as described above. The device may include a catheter, chest tube, syringe and needle.

EXAMPLE

Example 1

Patient A is an outpatient who has symptomatic pleural effusion. An indwelling pleural catheter is placed in his body. During his first visit to the clinic, the clinician removes 950 mL of fluid from his pleural space in 30 minutes. He returns to the outpatient clinic about every 24 hours.

| Day | Time of treatment | Amount of fluid removed |
| --- | --- | --- |
| 1 | 10:00 am | 950 mL |
| 2 | 9:00 am | 900 mL |
| 3 | 9:30 am | 825 mL |
| 4 | 10:15 am | 700 mL |
| 5 | 10:30 am | 575 mL |
| 6 | 10:00 am | 475 mL |
| 7 | 10:45 am | 200 mL |

After Day 7, having had two consecutive treatments where less than 300 mL of fluid was removed, Patient A returns to the clinic in 4 days to receive an eighth treatment, which removes 100 mL of fluid. The clinician determines that Patient A should come back to the clinic in two weeks, or sooner if symptoms arise.

What is claimed:

1. A method of treating pleural effusion in a subject, comprising:
   administering two or more first treatments comprising removing an amount of fluid from a pleural space of the subject at a rate of less than 600 mL/min using a pleural catheter, wherein the first treatments are administered at a frequency greater than 24 hours and less than 48 hours until 2 or more consecutive first treatments each remove less than 100 mL of fluid; and
   administering a sclerosing agent, wherein the pleural catheter elutes the sclerosing agent, and wherein after the 2 or more consecutive first treatments each removing less than 100 mL of fluid, the method further comprises one or more second treatments at a frequency of every more than 3 days, wherein the first treatments are same as the second treatments.

2. The method of claim 1, wherein the first treatments are administered at the frequency greater than 24 hours and less than 48 hours until 3 or more consecutive first treatments each remove less than 100 mL of fluid.

3. The method of claim 1, wherein the first treatments are administered at the frequency greater than 24 hours and less than 48 hours until 2 or more consecutive first treatments each remove less than 50 mL of fluid.

4. The method of claim 1, wherein the amount of fluid removed from the pleural space in at least one first treatment does not exceed 1.5 liters.

5. The method of claim 1, wherein the amount of fluid removed from the pleural space in at least one first treatment does not exceed 1 liter.

6. The method of claim 1, wherein the sclerosing agent is selected from the group consisting of: silver nitrate, $TGF_\beta$, talc, tetracycline, doxycycline, minocycline, doxorubicin, povidone iodine, and bleomycin.

7. The method of claim 1, wherein the sclerosing agent is silver nitrate.

8. The method of claim 1, wherein the rate of removing the amount of fluid from the pleural space of the subject is between 25 mL/min and 600 mL/min.

9. The method of claim 1, wherein the first treatments are administered for a duration of less than 2 hours.

10. A kit comprising:
a pleural catheter for removing fluid from a pleural space of a subject, and instructions for use, wherein the instructions for use comprise:
instructions to administer two or more first treatments comprising removing an amount of fluid at a rate of less than 600 mL/min from the pleural space of the subject using the pleural catheter, wherein the first treatments are administered at a frequency greater than 24 hours and less than 48 hours until 2 or more consecutive first treatments each remove less than 100 mL of fluid, and wherein after the 2 or more consecutive first treatments each removing less than 100 mL of fluid, one or more second treatments are administered at a frequency of every more than 3 days, wherein the first treatments are same as the second treatments; instructions to administer a sclerosing agent, wherein administration comprises the pleural catheter eluting the sclerosing agent.

11. The kit of claim 10, wherein the rate of removing the amount of fluid from the pleural space of the subject is between 25 mL/min and 600 mL/min.

12. The kit of claim 10, wherein the first treatments are administered for a duration of less than 2 hours.

* * * * *